US008586924B2

(12) United States Patent
Demos

(10) Patent No.: US 8,586,924 B2
(45) Date of Patent: Nov. 19, 2013

(54) ENHANCEMENT OF THE VISIBILITY OF OBJECTS LOCATED BELOW THE SURFACE OF A SCATTERING MEDIUM

(75) Inventor: Stavros Demos, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 357 days.

(21) Appl. No.: 12/880,376

(22) Filed: Sep. 13, 2010

(65) Prior Publication Data

US 2012/0062897 A1    Mar. 15, 2012

(51) Int. Cl.
G01N 21/55    (2006.01)

(52) U.S. Cl.
USPC ............ 250/336.1; 250/338.1; 250/341.8; 356/51; 356/432; 600/407; 600/473

(58) Field of Classification Search
USPC ......................................... 250/336.1
See application file for complete search history.

(56) References Cited

U.S. PATENT DOCUMENTS

| | | | | |
|---|---|---|---|---|
| 4,600,011 A | * | 7/1986 | Watmough | 600/475 |
| 4,807,637 A | * | 2/1989 | Bjorkholm | 600/476 |
| 5,137,355 A | * | 8/1992 | Barbour et al. | 356/342 |
| 5,497,769 A | * | 3/1996 | Gratton et al. | 600/323 |
| 5,931,789 A | * | 8/1999 | Alfano et al. | 600/473 |
| 6,032,070 A | * | 2/2000 | Flock et al. | 600/473 |
| 6,108,576 A | * | 8/2000 | Alfano et al. | 600/476 |
| 6,230,046 B1 | * | 5/2001 | Crane et al. | 600/476 |
| 6,665,557 B1 | * | 12/2003 | Alfano et al. | 600/473 |
| 7,006,676 B1 | * | 2/2006 | Zeylikovich et al. | 382/131 |
| 2004/0215081 A1 | * | 10/2004 | Crane et al. | 600/473 |
| 2005/0143662 A1 | * | 6/2005 | Marchitto et al. | 600/473 |
| 2005/0257795 A1 | * | 11/2005 | Hsiu-Chen et al. | 128/898 |
| 2006/0173360 A1 | * | 8/2006 | Kalafut et al. | 600/478 |
| 2006/0223032 A1 | * | 10/2006 | Fried et al. | 433/215 |
| 2007/0127118 A1 | * | 6/2007 | Nilson et al. | 359/385 |
| 2007/0134615 A1 | * | 6/2007 | Lovely | 433/29 |
| 2007/0276258 A1 | * | 11/2007 | Crane | 600/476 |

OTHER PUBLICATIONS

Demos et al., Optical polarization imaging; Applied Optics, vol. 36, No. 1, Jan. 1997.*

* cited by examiner

*Primary Examiner* — David Porta
*Assistant Examiner* — Djura Malevic
(74) *Attorney, Agent, or Firm* — John P. Wooldridge

(57) ABSTRACT

Techniques are provided for enhancing the visibility of objects located below the surface of a scattering medium such as tissue, water and smoke. Examples of such an object include a vein located below the skin, a mine located below the surface of the sea and a human in a location covered by smoke. The enhancement of the image contrast of a subsurface structure is based on the utilization of structured illumination. In the specific application of this invention to image the veins in the arm or other part of the body, the issue of how to control the intensity of the image of a metal object (such as a needle) that must be inserted into the vein is also addressed.

31 Claims, 5 Drawing Sheets

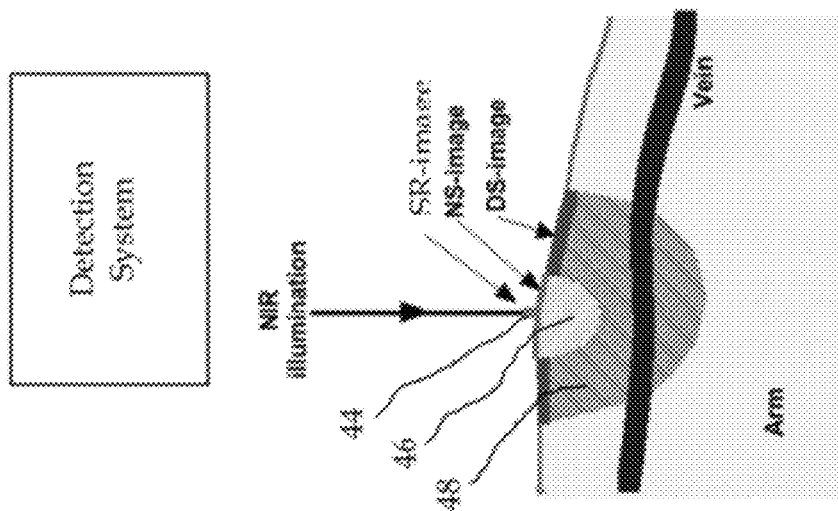
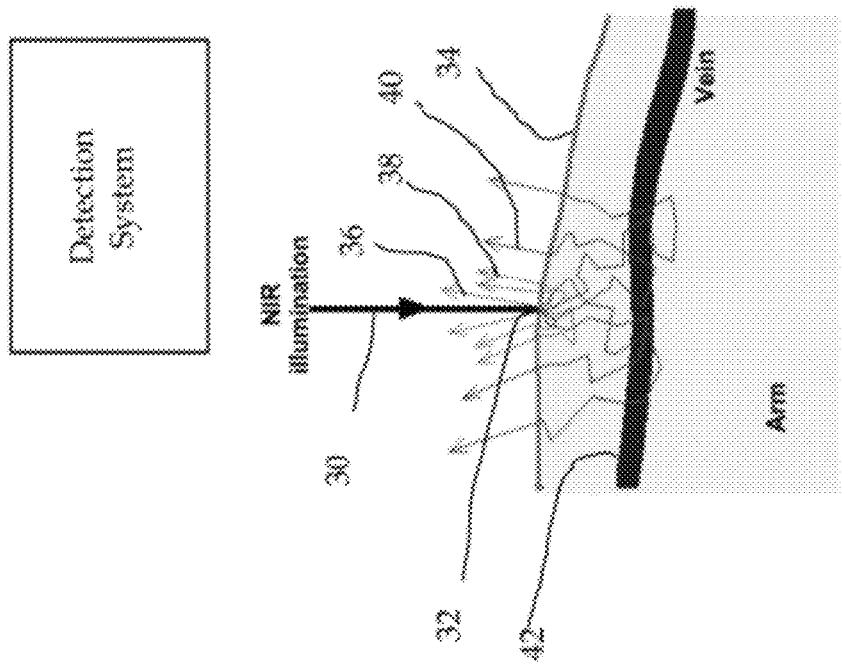

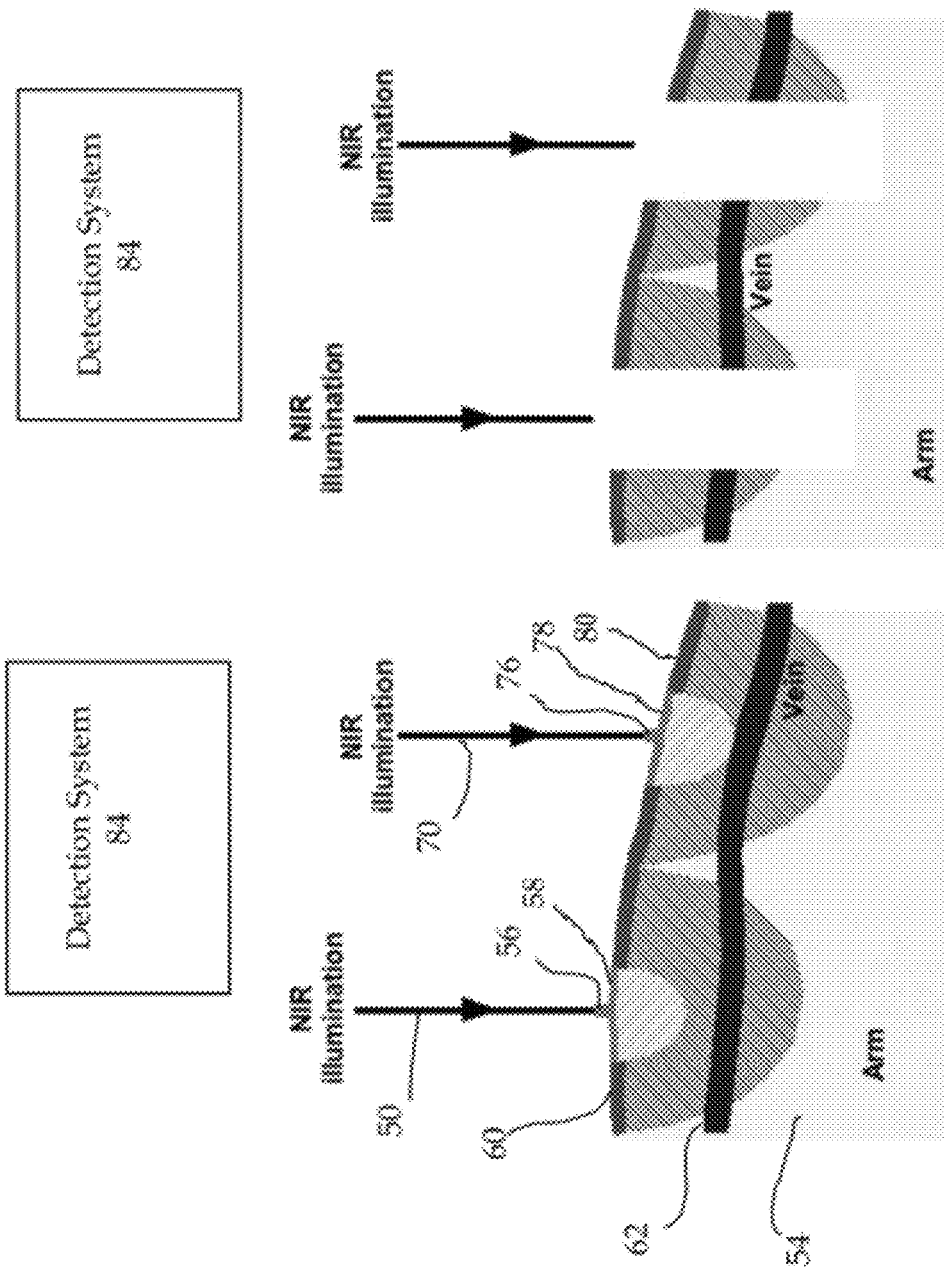

ENHANCEMENT OF THE VISIBILITY OF OBJECTS LOCATED BELOW THE SURFACE OF A SCATTERING MEDIUM

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to techniques for locating obscured objects, and more specifically, it relates to techniques for imaging objects located within a scattering medium.

2. Description of Related Art

Medical personnel often need to insert a needle or other similar devise in a near surface vein of a patient; however, it is often difficult to see or locate the vein and/or successfully insert the needle into the vein. This problem arises mainly due to the difficulty to visualize the vascular structures via observation with the naked eye because the ability of visible photons to penetrate the tissue is very limited. The use of infrared light to improve the visibility of the near surface vascular system is widely known. Reduced absorption of blood and myoglobin of the NIR spectral region allows a larger photon penetration depth of the NIR photons in the tissue. Photons in this spectral region can reach and interact with the subsurface veins such that images are formable from the detected NIR photons. Blood, however, remains the main absorbing chromophore, thus causing the veins to appear as darker features independently of the illumination wavelength.

The problem of visualizing the subsurface vascular system even with NIR light arises from that fact that still only a small portion of the light injected though the surface is able to reach the vein before being backscattered to reach the imaging devise. This process is depicted in FIG. 1. Specifically, upon the illumination with NIR light (from source 10) of the tissue (arm 12), a portion of the light 14 will be reflected at the interface between tissue and air due to the change in the index of refraction. The resulting image component (specular reflection image or SR-image) has no information on the spatial characteristics of the vein since it never interacted with the vein 16 of arm 12. The same is true for a second image component 18 that is composed of photons that only reached tissue depths shorter than the depth that the vein is located. The resulting image component (near subsurface or NS-image) is stronger than the third image component 20 (deep subsurface or DS-image) that is composed by photons that reached an adequate depth to interact with the vein. The DS-image bears information about the vein presence and geometrical characteristics and can be recorded by the imaging device 22. The relative intensity (strength) of the NS and DS image components depends on two parameters: i) the illumination wavelength (arising from the dependence of the reduced scattering coefficient based on the wavelength) and ii) the depth of the vein (since the number of photons that can a reach certain depth declines nearly exponentially with depth). As a result, if the vein is located deep enough below the surface, only a very small portion of the overall number of detected photons by the imaging device have interacted with the vein, which results in inadequate image contrast to visualize the vein. Therefore, in order to improve the ability to image the vein, the relative contribution of the DS image component must be increased. In previous work by Demos et al., methods were proposed to reduce or eliminate the SR and the NS image components. Specifically, since the SR image component is due to a single reflection event per detected photon, these photons maintain their polarization state. Therefore, using polarized illumination and detecting the orthogonal image components, the SR image component is at least partially eliminated. In order to remove the NS image component, the Spectral and Polarization Difference Imaging (SPDI) technique was proposed where the orthogonal polarization image components at two different wavelengths is used and subtracted after they are normalized so that the intensity of their corresponding NS image components is approximately equal. This subtraction provides the difference image of the remaining DS image components that are different in intensity due to the use of different wavelengths. It is desirable to overcome the degree of difficulty imposed by these prior art methods.

SUMMARY OF THE INVENTION

It is an object of the present invention to invention provide techniques for enhancing the visibility of objects located below the surface of a scattering medium. This and other objects will be apparent to those skilled in the art based on this disclosure.

Examples scattering media for purposes of this invention include tissue, water and smoke. Examples of such an object for purposes of this invention include a vein located below the skin, a mine located below the surface of the sea and a human in a location covered by smoke. Other media and objects usable for purposes of this invention will be apparent to those skilled in the art based on this disclosure. In some embodiments, the enhancement of the image contrast of a subsurface structure is based on the utilization of structured illumination. In the specific application of this invention, to image a vein in the arm or other part of the body, the issue of how to control the intensity of the image of a metal object (such as a needle) that must be inserted into the vein is also addressed. An exemplary technique for controlling the intensity of light reflected from a metal object creates ordered microstructures on the surface of the metallic or otherwise reflective needle, so that the light interacts with these microstructures in the same or a similar way that light interacts with a diffraction grating, in order to reflect the light towards the detector. Another exemplary technique for use with or without the ordered microstructures provides an additional side illumination source so that the light reflected from the metal can be directed into the imaging device. The invention has a variety of uses, including tissue imaging, imaging of veins, cancer imaging, lesion imaging and imaging in a scattering environment (e.g., sea, smoke, clouds, smog and fog). Embodiments of the invention utilize image reconstruction after acquiring images using different patterns of structured illumination.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 2A shows example propagation paths of reflected near infrared light from the surface of skin and scattered near infrared light from under the surface of an arm to a detection system.

FIG. 2B shows example propagation zones of reflected near infrared light from the surface of skin and scattered near infrared light from under the surface of skin.

FIG. 3A shows examples of two propagation zones of reflected near infrared light from the surface of skin and scattered near infrared light from under the surface of skin.

FIG. 3B shows examples of two eliminated propagation zones of reflected near infrared light from the surface of skin and scattered near infrared light from near the surface of skin.

DETAILED DESCRIPTION OF THE INVENTION

Figure 1:
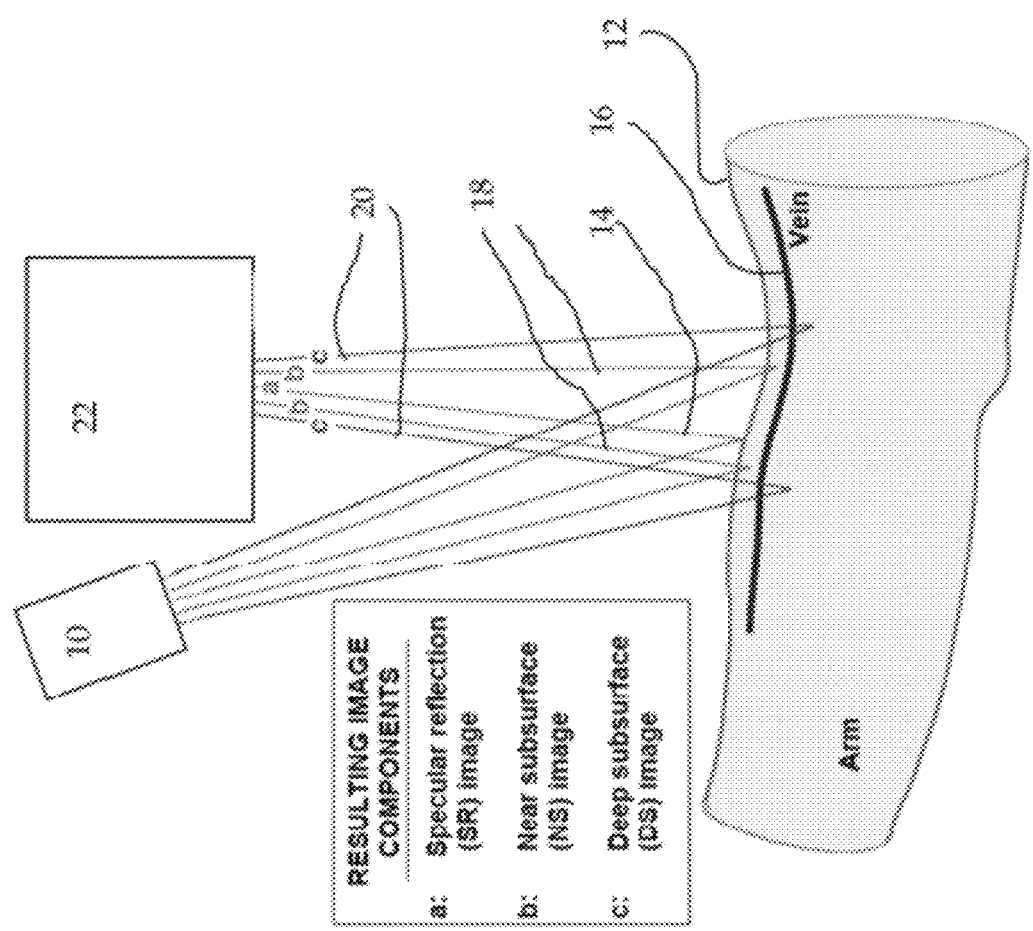
FIG. 1 shows example propagation paths of near infrared light from an arm to a detection system.

To appreciate the basic principles of this invention, one can consider the way light interacts with tissue to produce the three image components as described above (SR-, NS- and, DS-images). Referring to FIG. 2A and assuming that the illumination 30 is delivered to only one point 32 (or small area) on the tissue surface (skin) of arm 34, the SR image component 36 will be produced only from the area directly exposed to the light source. On the other hand, the NS image components 38 and DS image components 40 will expand beyond the area of direct illumination because the scattering of light taking place inside the tissue will expand the area (volume) that light will reach and interact with tissue. In principle, the photons that reach larger penetration depth undergo a larger number of scattering events and as a result, their average distance from the point where they were injected to the point where they emerge from the tissue increases. Consequently, the photons comprising the DS image component cover a larger area of the tissue than those comprising the NS image component. FIG. 2A further shows that the DS components propagate deep enough into the tissue to interact with vein 42. FIG. 2B shows the generalized SR interaction region 44, the generalized NS interaction region 46 and the generalized DS interaction region 48 of the SR, NS and DS components, respectively. The figure also shows, on the surface of the skin, the SR, NS and DS images.

Assume that the arm is illuminated in only appropriately arranged discrete locations with each location covering only a portion of the entire tissue surface area as shown in FIG. 3A. The figure shows NIR light 50 directed onto the surface of arm 54 to produce SR light 56, NS light image 58 of and DS light image 60. The zone of DS light is shown to interact with vein 62. The figure also shows NIR light 70 directed onto the surface of arm 54 to produce SR light 76, NS light image 78 and DS light image 80. The DS light is shown to interact with vein 62. The figure also shows a detection system 84. In this case, there will be a large portion of the arm where the emerging photons as recorded by the imaging devise are predominantly those that reached larger penetration depths, thus the image will be composed predominantly by the DS-image type. The image intensity of these areas would be lower but these areas as imaged have a higher relative content of the DS image type, which contains image information of tissue structures located deep into the tissue, namely the deeper veins. Thereafter, one can utilize image processing so that the imaged area that contains pixel intensity higher than a predetermined value (threshold) will be digitally zeroed as shown in FIG. 3B. More specifically, FIG. 3B shows identical elements with the exception that the SR and NS image components have been zeroed from the detected image. Image processing techniques for digitally zeroing the image area that contains pixel intensity higher than a predetermined value are known in the art. Examples of such techniques include the use of computer software and hardware, and can also simply include the use of one or more physical apertures or masks. Other techniques will be apparent to those skilled in the art based on this disclosure. This will leave an image of the tissue surface that has areas that are blank but the areas with recorded signal are predominantly (or contain enhanced content) of the DS type. Subsequently, the pattern of discrete locations where the illumination is delivered will be changed so that a new predominantly DS type image will be recorded covering a different portion of the tissue surface. By recording an appropriate number of images in this fashion and using an appropriate image reconstruction algorithm (which can be as simple as image addition), an image of the arm that is predominantly of DS type will be obtained. This image will provide enhanced contrast of the deep subsurface structures such as veins. Note also that although FIGS. 2A through 3B show the NIR directed onto the normal of the tissue, it is advantageous in some cases to direct the input beam at an angle greater than the normal so that the image that propagates to the surface will be displaced from the input area.

The same method can be used to detect objects located in a different type of scattering medium. For example, an airplane can scan a body of water while it records images of the reflected light. These images can be then reconstructed to maintain the DS image component and remove the NS and SR components.

Figure 4B:
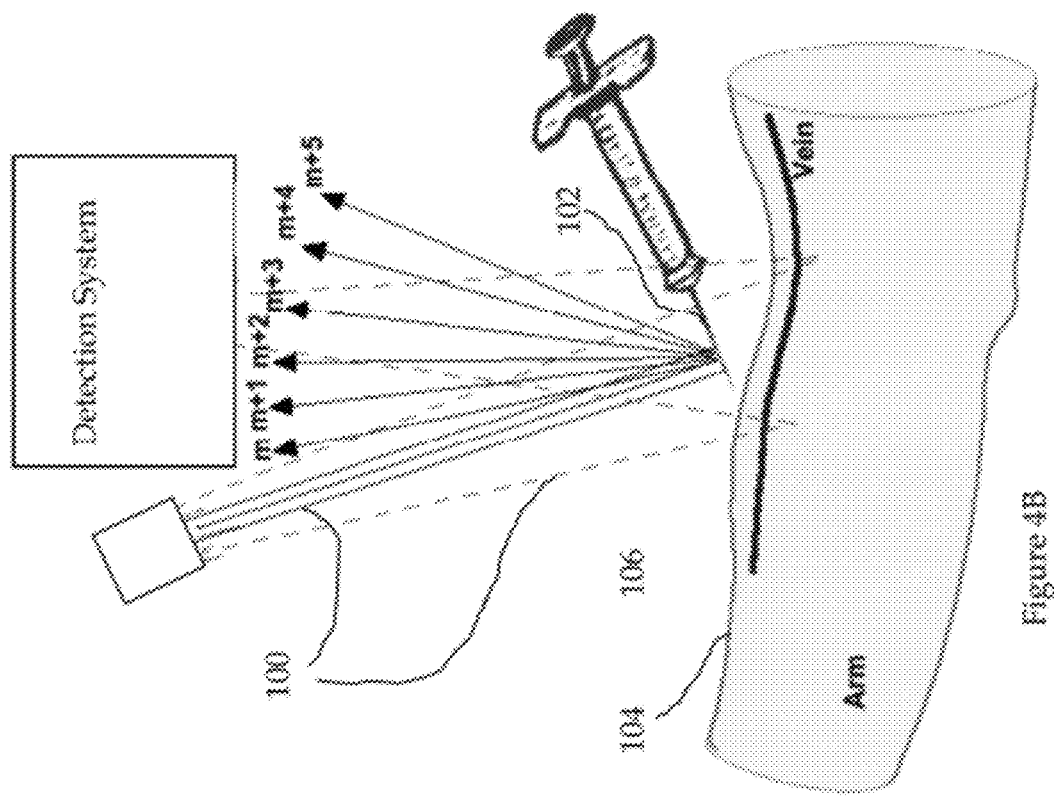
FIG. 4B shows example reflected orders from a reflection grating blazed onto the surface of a needle.
Figure 4A:
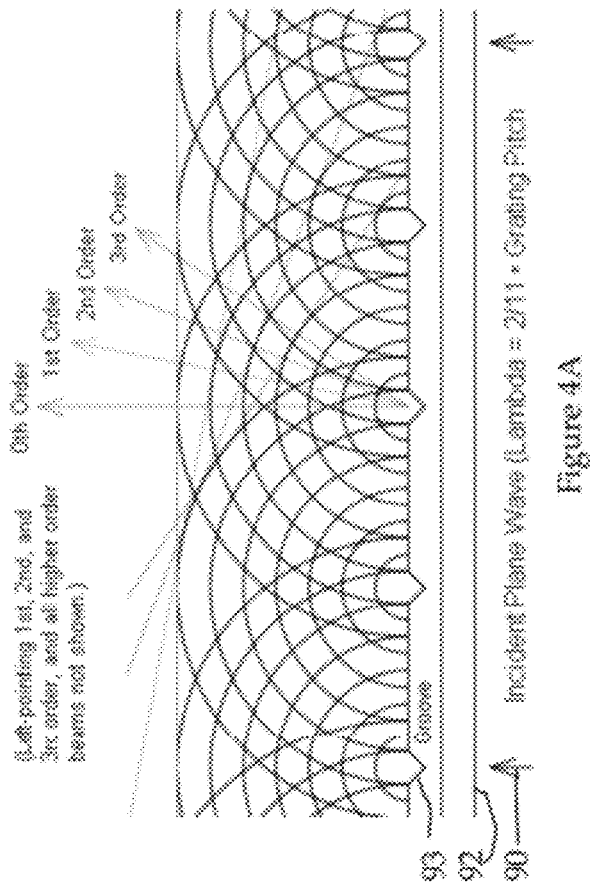
FIG. 4A shows an example of some transmitted orders from a transmission grating.

For imaging of, e.g., the near surface vascular system, embodiments of this invention include means for controlling the intensity of the image of a metal object (such as a needle) that must be inserted into the vein. During conventional visual inspection of the arm (or other part of the body) to locate the vein, the needle is visible to the operator due to ambient multidirectional illumination, although the reflection of light from the needle is mainly specular. This is because there will always be light photons that have the correct direction to reach the observer or the detection system following specular reflection from the needle. When the illumination becomes omni directional (such as in this invention or in other type of configurations where light from an NIR illumination source is used to enhance the visibility of the near surface vascular system), specular reflection on the needle will lead to mostly reflection of the light away from the imaging devise thus making the needle a dark object (invisible). To address this problem, an aspect of this invention creates ordered microstructures on the metal surface of the needle, e.g., so that the light interacts with these microstructures in the same or in a similar way that it does with a diffraction grating, in order to ensure that there will always be a portion of the illumination light directed towards the imaging device (such as a CCD or MOS detector). A diffraction grating is a reflecting or transparent element, whose optical properties are periodically modulated. Diffraction gratings often comprise fine parallel and equally spaced grooves or rulings on the surface of a material. When light is incident on a diffraction grating, diffractive and mutual interference effects occur, and light is reflected or transmitted in discrete directions, called diffraction orders. This effect is depicted in FIG. 4A. When beam 90 is incident on a grating (in this case a transmission grating 92) with an angle θi (measured from the normal of the grating), it is diffracted into several beams. The beam that corresponds to direct transmission (or specular reflection in the case of a reflection grating) is called the zero order, and is denoted m=0 or the $0^{th}$ order. The other orders correspond to diffraction angles which are represented by non-zero integers m. In addition to the $0^{th}$ order, the figure shows only the $1^{st}$ order, the $2^{nd}$ order and the $3^{rd}$ order. The angles of the diffracted orders only depend on the period of the grooves (in this case, grooves 93), and not on their shape. A triangular shape profile is commonly used. This technique is called blazing. The incident angle and wavelength for which the diffraction is most efficient are often called blazing angle and blazing wavelength.

Such technology can be incorporated on specially manufactured needles suitable for the application of improving the visibility of the a needle, which is especially important after it has been inserted into the tissue. The blazing on the needle surface can be done by shaping the surface of the metal (using mechanical means or other methods such as lasers) and then the surface may be coated by a transparent material to re-establish a smooth surface. Other technologies known in the art for grating fabrication can be used to introduce the diffraction properties on a coating covering a needle surface. Such technology may be based on fabrication techniques for producing volume phase holography diffraction gratings or even simpler technologies that approximate the diffraction effects observed on ordinary pressed CD and DVD media. The application of this approach is demonstrated in FIG. 4B wherein a NIR beam 100 is incident of a needle 102 that includes a periodic structure on its surface. The periodic structure reflects light into a series of orders. The figure shows the $0^{th}$ order through the $5^{th}$ order. The figure also shows the NIR light incident onto arm 104, which includes vein 106. When the needle is inserted into the arm, the DS light will image the needle as well as the vein, allowing the needle to be directed into the vein.

Figure 5:
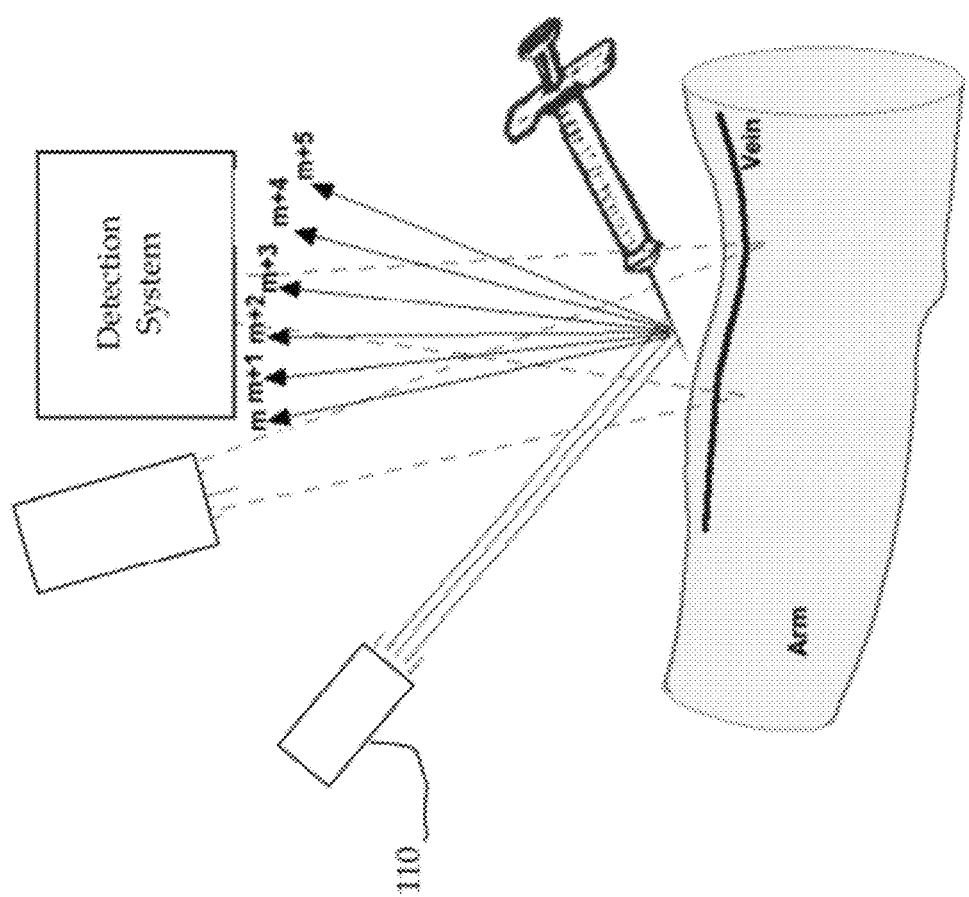
FIG. 5 shows a second illumination source directed at a reflection grating blazed onto the surface of a needle.

The above describe visibility problem can also be addressed through the use of a second illumination source. FIG. 5, includes identical elements as the elements shown in FIG. 4B and further includes the second illumination source 110. This second illumination light is directed above the surface to be imaged and onto the needle. A benefit of using a second illumination source is that the intensity of the needle in the final image recorded by the detection system can be adjusted by the operator. It must be noted that in this specific configuration, the needle can simply be roughened (abraded) so that the light from the specularly reflected light from the needle surface originating from the second illumination source is directed in a wide range of angles (and therefore a portion of that light reaches the imaging device). This second illumination source can be further equipped with a polarization element to control the polarization state of the light detected by the imaging system. This is particularly useful for the case where the imaging of the subsurface vascular system incorporates the use of polarization elements as described for example in Demos et al., "Optical Polarization Imaging," Applied Optics, 36, 150-155, 1997, R. R., incorporated herein by reference; Alfano and S. G. Demos, "Imaging of Objects Based Upon the Polarization or Depolarization of Light", U.S. Pat. No. 5,929,443, incorporated herein by reference; and R. R. Alfano and S. G. Demos, "Imaging of Objects Based Upon the Polarization or Depolarization of Light", U.S. Pat. No. 5,847,394, incorporated herein by reference.

Some embodiments of the invention include a method, comprising: (i) injecting electromagnetic radiation (EMR) into a medium such that some of the EMR propagates into the medium, where if an object is located within the path of the EMR in the medium, a shadow of the object will be produced; and (ii) detecting the shadow to produce at least one detected shadow. The area is often about where the EMR meets the medium. The area is often about an interface where the EMR meets the medium. The medium comprises a scattering medium. A spatial map of the object is formed from the at least one detected shadow. The EMR comprises at least one of an intensity and a wavelength sufficient to propagate to at least one depth within the object to produce the at least one shadow of the object. The EMR often comprises near infrared (NIR) light and more specifically, the NIR light often comprises a wavelength within a range from about 0.75 μm to about 1.4 μm. Generally, the EMR comprises near infrared (NIR) light, where a first part of the NIR light is reflected from the interface of the medium to produce specularly reflected (SP) light, where a second part of the NIR light propagates into the medium to produce near surface (NS) scattered light and where a third part of the NIR light propagates into the medium to produce deep surface (DS) scattered light and where the at least one shadow is formed when the DS scattered light is attenuated or blocked by the object. The method generally further comprises eliminating a portion of at least one of the SP light and the DS light. A second portion of EMR is often injection into the medium, where if a second part of the object is located within the path of the second EMR in the medium, the at least one shadow will comprise a second shadow of the object will be produced, in which case the second shadow is detected to produce a second detected shadow. The at least one detected shadow is imaged to produce at least one image. The EMR is often configured in a structured pattern. The object comprises an index of refraction that is different from that of the medium. The method may further comprise propagating the EMR to a series of areas about where the EMR meets the medium, in which case the method further comprises detecting an image at each area of the series of areas. The method often further comprises observing the at least one image while inserting at least one element into the medium. The element can comprise a periodic structure on a surface of the at least one element. The periodic structure can be a diffraction grating and the element can be a hypodermic needle. The EMR can be injected into the medium at a plurality of angles. Examples of the medium can be tissue, smoke, dust, gas and liquid. The method can further comprise imaging the at least one image of the at least one shadow to produce at least one image, where the step of eliminating the portion comprises digitally zeroing portions of the at least one image that contain pixel intensity higher than a predetermined value. The invention includes embodiments of apparatuses that carry out the methods of the invention. Generally, apparatuses of the invention can include (i) a means for injecting electromagnetic radiation (EMR) into a medium such that some of the EMR propagates into the medium, where if an object is located within the path of the EMR in the medium, a shadow of the object will be produced; and a means for detecting the shadow to produce at least one detected shadow.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:

1. A method, comprising:
   providing a scattering medium that includes an internal structure of interest;

injecting electromagnetic radiation (EMR) into said medium at an entry location such that some of said EMR propagates into and is scattered by said medium to produce scattered EMR, wherein a portion of said scattered EMR exits said medium at an exit location to produce signal light, wherein said entry location and said exit location have no union; and collecting at least a portion of said signal light, while excluding all light exiting and reflecting from said entry location, to produce collected light for producing an image of said internal structure of interest.

2. The method of claim 1, wherein said entry location is about where said EMR meets said medium.

3. The method of claim 1, wherein said entry location is about an interface where said EMR meets said medium.

4. The method of claim 1, further comprising,
injecting said EMR into said medium at a second entry location such that some of said EMR propagates into and is scattered by said medium to produce second scattered EMR, wherein a portion of said second scattered EMR exits said medium at a second exit location to produce second signal light, wherein said second entry location and said second exit location have no union; and collecting at least a portion of said second signal light, while excluding all EMR exiting or reflecting from said second entry location, to produce second collected light for forming said image of said internal structure of interest; and combining said first collected light and said second collected light to produce said image of said internal structure of interest.

5. The method of claim 4, further comprising forming a spatial map of said internal structure of interest from said image.

6. The method of claim 4, wherein said EMR is configured in a structured pattern.

7. The method of claim 6, wherein said structured pattern comprises a geometrical shape selected from a group consisting of a line, a set of crossing lines, a circle and a point like area.

8. The method of claim 4, further comprising observing said image of said internal structure of interest while inserting at least one element into said medium, wherein said EMR is provided from a first illumination source, wherein the step of observing said image of said internal structure of interest includes illuminating said at least one element with light from a second illumination source to produce at least one image of said at least one element as it is being inserted into said medium.

9. The method of claim 8, wherein said element comprises a periodic structure on a surface of said at least one element.

10. The method of claim 9, wherein said periodic structure is configured to produce a diffraction pattern.

11. The method of claim 8, wherein said at least one element comprises a hypodermic needle.

12. The method of claim 8, wherein said EMR is injected into said medium at a plurality of angles.

13. The method of claim 4, wherein said image is formed by superposition and/or digital processing of the images containing the signal.

14. The method of claim 1, wherein said EMR comprises at least one of an intensity and a wavelength sufficient to propagate to at least one depth within said medium to interact with said internal structure of interest.

15. The method of claim 1, wherein said EMR comprises near infrared (NIR) light.

16. The method of claim 15, wherein said NIR light comprises a wavelength within a range from about 0.75 μm to about 1.4 μm.

17. The method of claim 1, wherein said EMR comprises near infrared (NIR) light, wherein a first part of said NIR light is reflected from said medium to produce specularly reflected (SP) light, wherein a second part of said NIR light propagates into said medium to produce near surface (NS) scattered light and wherein a third part of said NIR light propagates into said medium to produce deep surface (DS) scattered light, wherein said image of said internal structure of interest is formed when said scattered EMR originating from DS scattered light is attenuated or blocked by said object.

18. The method of claim 17, further comprising eliminating a portion of at least said SP light and said NS light.

19. The method of claim 1, wherein said internal structure of interest comprises a complex index of refraction that is different from that of said medium.

20. The method of claim 1, wherein said entry location comprises a plurality of entry locations and wherein said exit location comprises a plurality of exit locations, wherein each exit location corresponds to a single unique entry location, the method further comprising collecting light from each exit location of said plurality of exit locations to produce a plurality of respective collected light signals while simultaneously excluding from said collected light signals all light reflected from or exiting from each respective entry location; and forming an image by combining all said collected light signals.

21. The method of claim 1, wherein said EMR is injected onto said medium in a line.

22. The method of claim 1, wherein said medium is selected from the group consisting of tissue, smoke, dust, gas and liquid.

23. The method of claim 1, wherein the step of injecting EMR includes scanning said EMR across the surface of said medium, wherein the step of collecting at least a portion of said signal light includes collecting signal light as said EMR is being scanned.

24. The method of claim 1, wherein said EMR is injected in as a geometrical structure that is varied in time, wherein the step of collecting at least a portion of said signal light includes collecting sign light as said geometrical structure is varied in time.

25. The method of claim 1, wherein the step of collecting at least a portion of said signal light includes collecting signal light with an imaging sensor or a point detector.

26. The method of claim 1, wherein the step of excluding all light exiting and reflecting from said entry location includes digitally zeroing said all light exiting end reflecting from said entry location.

27. The method of claim 26, where the stet of digitally zeroing comprising setting a threshold value at and above which the pixel intensity is set to zero.

28. The method of claim 1, wherein the step of excluding all light exiting and reflecting from said entry location comprises using spatial filtering to exclude said all light exiting and reflecting from said entry location.

29. The method of claim 1, wherein the step of injecting EMR includes exposing the entire area of interest to varying illumination patterns, wherein the step of collecting includes capturing images of said entire area of interest.

30. A method, comprising:
injecting electromagnetic radiation (EMR) into a medium such that some of said EMR propagates into said medium, wherein if an object is located within the path of said EMR in said medium, a shadow of said object will be produced, wherein said EMR comprises near infrared (NIR) light, wherein a first part of said NIR light is reflected from said interface of said medium to produce specularly reflected (SP) Light, wherein a second part of said NIR light propagates into said medium to produce near surface (NS) scattered light and wherein a third part of said NIR light propagates into said medium to produce deep surface (DS) scattered light, wherein said at least one shadow is formed when at least a portion of said DS scattered light is attenuated or blocked by said object;

eliminating portion of at least one of said SP light and said NS light; and imaging at least a portion of said at least one shadow to produce at least one image, wherein the step of eliminating said at least a portion of said at least one shadow comprises digitally zeroing portions of said at least one image that contain pixel intensity higher than a predetermined value.

31. An apparatus, comprising:

means for injecting electromagnetic radiation (EMR) into a scattering medium at an entry location, wherein said scattering medium includes an internal structure of interest such that some of said EMR propagates into and is scattered by said medium to produce scattered EMR, wherein a portion of said scattered EMR exits said medium at an exit location to produce signal light, wherein said entry location and said exit location have no union; and means for collecting at least a portion of said signal light, while excluding all light exiting and reflecting from said entry location, to produce first collected light for producing an image of said internal structure of interest.

* * * * *